United States Patent [19]

Vinegar et al.

[11] Patent Number: 4,663,711

[45] Date of Patent: May 5, 1987

[54] METHOD OF ANALYZING FLUID SATURATION USING COMPUTERIZED AXIAL TOMOGRAPHY

[75] Inventors: Harold J. Vinegar; Scott L. Wellington, both of Houston, Tex.

[73] Assignee: Shell Oil Company, Houston, Tex.

[21] Appl. No.: 623,297

[22] Filed: Jun. 22, 1984

[51] Int. Cl.⁴ ......................... G01V 1/00; A61B 10/00
[52] U.S. Cl. ................................... 364/420; 364/422; 378/901; 128/660
[58] Field of Search ............... 364/400, 421, 422, 414; 378/901; 128/660

[56] References Cited

U.S. PATENT DOCUMENTS

| | | | |
|---|---|---|---|
| 4,331,877 | 5/1982 | Barrett et al. | 364/414 X |
| 4,493,039 | 1/1985 | Gregory | 364/414 |
| 4,542,648 | 9/1985 | Vinegar et al. | 73/153 |
| 4,562,540 | 12/1985 | Devancy | 250/256 X |

Primary Examiner—Jerry Smith
Assistant Examiner—Charles B. Meyer

[57] ABSTRACT

A method using computerized axial tomography (CAT) to model flood performance in a petroleum reservoir using model rock or core from the reservoir of interest. The method uses X-rays of two different energy levels and dopes one of the fluids in the core with a strong photoelectric absorbing material. Multiple scans are conducted at the two energy levels during the displacement process. The resulting data permits calculation of the oil, water and gas phase saturations.

10 Claims, 3 Drawing Figures

SATURATION AFTER 0.03 PV $CO_2$ INJECTION

METHOD OF ANALYZING FLUID SATURATION USING COMPUTERIZED AXIAL TOMOGRAPHY

BACKGROUND OF THE INVENTION

This invention relates to computerized axial tomographic (CAT) analysis and, more particularly, to the determination of the spatial distribution of three phases, i.e., water, oil and gas in a sample, such as a core sample from a borehole during fluid flow through the core. The saturation of the three phases in the sample can be measured dynamically during a laboratory displacement process.

The determination of three-phase saturations by computerized axial tomography (hereinafter referred to as "CAT") is based on the fact that X-ray attenuation depends both on the density and the chemical composition of a material. For mean energies above about 100 keV X-rays interact with matter predominantly by Compton scattering which is dependent on electron density. For X-ray energies below a mean energy of 100 keV, photoelctric absorption becomes important; this type of interaction is strongly dependent on atomic number.

The prior art has suggested the use of X-rays for measuring oil saturation in rock cores. These methods have all related to two-phase flow and used a single X-ray energy and an average measurement over a cross section of the core. The resulting displays were one dimensional and do not provide information relating to discrete variation in the flow pattern across the section. The prior art has also suggested use of CAT to obtain a two dimensional plot of fluid movement through the core. The prior use of CAT has been two-phase single energy X-ray scanning of the core under atmospheric temperature and pressure.

SUMMARY OF THE INVENTION

In accordance with the present invention there is provided a method for making laboratory measurements which model reservoir performance during primary, secondary, and tertiary processes.

The method can be applied either to typical model rocks, such as Berea sandstone, or to actual core from the reservoir of interest. The order in which steps are performed in this method depends on whether model rock or preserved core are used. Preserved core is the preferred embodiment because the actual downhole conditions are most closely duplicated, such as surface wettability, crude oil composition, and the distribution of the crude oil among the pore sizes. However, preserved core is not always available, and the procedures described below are somewhat more laborious than when model rocks are used. In addition, the reservoir engineer is often interested in the typical performance of a recovery process, rather than the performance on a particular rock.

The saturation of the brine, oil, and gas phases can be determined by making two scans at different X-ray energies, e.g. at 90 and 120 KVp (peak kilovoltage). The saturation of each phase is then determined from the following equations:

$$\mu_1 = \mu_{o1}S_o + \mu_{w1}S_w + \mu_{g1}S_g \quad (1)$$

$$\mu_2 = \mu_{o2}S_o + \mu_{w2}S_w + \mu_{g2}S_g \quad (2)$$

$$1 = S_o + S_w + S_g \quad (3)$$

In the above expression $\mu$ is the total attenuation coefficient for the core with multiple phases present and the terms $\mu_o$, $\mu_w$ and $\mu_g$ are attenuation coefficients for the core 100% saturated with oil, water and gas. $S_o$, $S_w$ and $S_g$ are the respective saturations. The subscripts 1 and 2 refer to the high and low X-ray energies used.

The invention can be carried out using either an actual reservoir core sample or a model rock such as Berea sandstone. In either case a sample is prepared, mounted and disposed in a CAT scanner similar to that described in the copending application of the same inventors and which is assigned to the same assignee as the present application; copending Application Ser. No. 566,618 filed Dec. 29, 1983 and now U.S. Pat. No. 4,571,491. The system described in that copending application provides a means for disposing a sample in an aluminum pressure vessel and then subjecting the sample to pressures and temperatures corresponding to the pressures and temperatures of the reservoir of interest. The system also provides means for automatically scanning the sample at different X-ray energy levels. The measurements are taken at a series of positions along the core as described in the copending application.

BRIEF DESCRIPTION OF THE DRAWINGS

The present invention will be more easily understood from the following description when taken with the attached drawings in which.

DETAILED DESCRIPTION OF THE PREFERRED EMBODIMENTS

Figure 1:
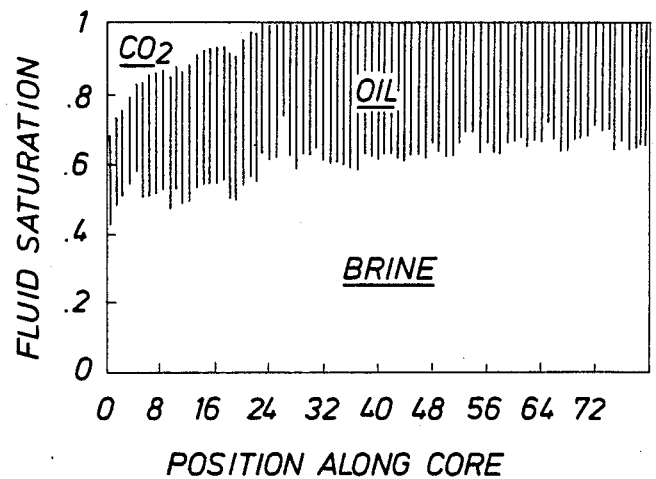
FIG. 1 shows the fluid saturation obtained using the present invention and CAT measurements.

The energy dependence of the X-ray linear attenuation coefficient $\mu$ is separated into two parts:

$$\mu = \mu_p + \mu_c \quad (4)$$

where $\mu_c$ is the Klein-Nishina function for Compton scattering multiplied by electron density, and $\mu_p$ represents photoelectric absorption (including coherent scattering and binding energy corrections). The photoelectric and Compton contributions can be expressed in the form:

$$\mu = aZ^m\rho + b\rho \quad (5)$$

where Z is the atomic number, m is a constant in the range of 3.0 to 4.0, $\rho$ is the electron density, and a and b are energy-dependent coefficients.

The present invention determines the saturation of the three phases in the sample by doping one of the phases present in the sample with a strong photoelectric absorbing material such as iodine or tungsten. For example, the oil phase may be doped with iodododecane while the brine phase can have dissolved sodium or potassium iodides or sodium tungstate as the doping agent. Similarly, the gas phase could be doped with xenon or krypton gas. Doping one of the phases with a strong photoelectric absorbing material substantially increases the response of this phase to the low energy X-ray. The iodated oil is chosen to match the properties of the original crude oil in the core as to phase behavior and mixing with the solvent. An alternate method would be an oil phase consisting of only iodododecane or a mixture of iodated oils. Thus, when the sample is scanned with low energy X-rays the resulting measurements will be primarily the response of the doped phases present in the sample. Whichever phase is doped will be the phase whose saturation is determined most accurately. The X-ray energies are chosen so that the higher energy is sensitive to Compton scattering processes while the low energy is sensitive to photoelectric absorption. The dual energies are achieved either by changing the peak acceleration voltage applied to the tube, or by appropriate filters placed in the beam, or by a combination of these methods.

With model rock, the method consists of the following steps. The rock is machined into cylindrical shape, then cleaned with chloroform/methanol azeotrope to remove hydrocarbons and salts. The rock is then mounted inside a thin shrinkable Teflon tube, which is heat-shrunk against the rock. The Teflon-encased core is then inserted inside a tight-fitting rubber sleeve, preferably constructed of Buna-N rubber for low X-ray attenuation. The rubber-jacketed core is mounted inside the aluminum pressure vessel shown in U.S. Pat. No. 4,571,491 filed Dec. 29, 1983. The pressure vessel is then heated by means of the Minco foil heaters to the formation temperature, and formation confining pressure is applied.

The CAT images obtained at each stage are stored to an appropriate medium, such as magnetic tape or disc. The stored data can be processed later on either by the CAT or a larger mainframe computer for rapid computation of saturation in equations (6)-(8). Longitudinal reconstructions can be made in the vertical and horizontal planes, i.e., sagittal and corona reconstructions.

The rock is initially fully saturated with gas. Multiple cross-sectional CAT images are obtained down the length of the core using two different X-ray energies. This condition is $S_g = 1$ which is used in equations (6)-(8) to calibrate $\mu_{g1}$ and $\mu_{g2}$.

The core is now flooded with brine, and imaged as above. This condition is $S_w = 1$ which is used in equations (6)-(8) to calibrate $\mu_{w1}$ and $\mu_{w2}$. The injection rate and fluid production rate are monitored throughout the flooding steps disclosed below. The oil phase is now injected into the core, and the set of dual-energy CAT cross-sections is again obtained, together with vertical and horizontal reconstructions. These images correspond to the initial oil saturation, $S_{oi}$. The core is then waterflooded to $S_{orw}$, (residual oil after waterflood), and scanned as above. The tertiary displacement process is then initiated, which can be, for example, a miscible $CO_2$ injection. The core is imaged a plurality of times during this injection to observe the time history of the displacement.

The final step is the cleaning and extraction of the core, using for example, a Soxhlet or Dean-Stark extraction process, resaturating the core with the oil phase occupying 100% of the pore volume, and reimaging the core. This condition is $S_o = 1$ which is used in equations (6)-(8) to calibrate $\mu_{o1}$ and $\mu_{o2}$. An alternate procedure for obtaining the $S_o = 1$ image is to utilize the $S_{orw}$ and $S_{oi}$ images and the known average values of $S_{orw}$ and $S_{oi}$ from the effluent fluids. Then a linear regression between values of measured attenuation at $S_o = 0$, $S_{orw}$, and $S_{oi}$ can be extrapolated to give $\mu_{o1}$, $\mu_{o2}$ without having to clean and resaturate the core with oil.

The three-phase saturation in any pixel of either the cross-sectional or longitudinal images is then computed using the equations:

$$\mu_1 = \mu_{o1}S_o + \mu_{w1}S_w + \mu_{g1}S_g \tag{6}$$

$$\mu_2 = \mu_{o2}S_o + \mu_{w2}S_w + \mu_{g2}S_g \tag{7}$$

$$1 = S_o + S_w + S_g \tag{8}$$

where (1,2) refer to the two X-ray energies. $S_o$, $S_w$, and $S_g$ are the oil phase, brine phase, and gas phase saturations, respectively, and $\mu_o$, $\mu_w$, $\mu_g$ are the measured linear attenuation coefficients when the core is 100% saturated with the oil phase, brine phase, and gas phase, respectively. The 6 coefficients $\mu_{o1}$, $\mu_{w1}$, $\mu_{g1}$, $\mu_{o2}$, $\mu_{w2}$, $\mu_{g2}$ are determined from the calibration scans as explained above.

As an alternate method of determining the 6 coefficients in equations (6) and (7), they can be calculated from literature values of mass attenuation coefficient and knowledge of the X-ray spectrum. This eliminates the need to obtain separate $S_o = 1$, $S_w = 1$ and $S_g = 1$ images.

The advantages of this invention are that reservoir sweep and displacement efficiency can be independently measured, in contrast with existing laboratory fluid flow techniques where only total recovery efficiency is measured. In addition, the vertical and horizontal reconstructions separate the effects of gravity on the displacement. When the Computerized Tomography images are compared with numerical simulations, the effects of viscous and capillary forces can be independently determined. Still another advantage is that both longitudinal and transverse dispersion coefficients can be measured. Yet another advantage is the measurement of the non-wetting phase trapping curve. Another advantage is the observation of core wettability from capillary end effects which occur during fluid flow. Further, the laboratory results of three-phase CAT saturation measurements can be easily scaled to reservoir conditions. For laboratory results to be applicable to reservoir conditions the sample must be properly scaled, i.e., the ratio of the diameter and length of the sample must be approximately the same as the ratio of the height and length of the formation. With a one-to-one correspondence the CAT scanning allows quantitative analysis of process variables under reservoir conditions. The viscosity and composition of the fluids can be controlled and if the sample is properly scaled the gravitational to viscous forces will be correct.

If preserved core is utilized rather than model rocks, the method of this invention is similar but carried out in a different order. The preferred core material is frozen core from the zone of interest, drilled either parallel or perpendicular to the core axis. The perpendicular direction is preferred because this represents the direction of fluid flow in the formation. However, this will limit the length of specimen to approximately 3-6 inches. The frozen core is machined into cylindrical shape while frozen at liquid nitrogen temperatures. The frozen cylindrical core is inserted into a tight fitting rubber sleeve, and mounted in the aluminum pressure vessel. The core is scanned with dual energies as above before it is allowed to thaw. The core is allowed to thaw in place, and a very slow flood (approximately 1 ft/day frontal advance rate) of doped brine is initiated. In this case use of doped brine is preferable because the reservoir oil should not be modified. After equilibrium is reached, i.e., no further change in linear attenuation coefficient is observed, the core is fully scanned and the CAT images will correspond to $S_{orw}$ conditions from which residual oil saturation will be determined. Reservoir crude and brine can now be simultaneously injected for three-phase relative permeability measurements. Finally, the tertiary floods are performed as above for model rock.

After secondary and tertiary flooding, the core is cleaned with a solvent, such as an alcohol, toluene, or chloroform/methanol azeotrope. The core is then imaged fully gas saturated ($S_g=1$) to calibrate $\mu_{g1}$ and $\mu_{g2}$, then flooded with doped brine to $S_w=1$ and reimaged to calibrate $\mu_{w1}$ and $\mu_{w2}$. The core is then cleaned again with a solvent to extract the brine and salts, then dried with dry nitrogen gas, and finally resaturated to $S_o=1$ with reservoir crude or reconstituted reservoir crude to calibrate $\mu_{o1}$ and $\mu_{o2}$. Thus, in the case of preserved core material, the calibration images needed to compute the three-phase saturations are obtained after the core floods, rather than before as in the case using model rock. The three-phase saturations are computed in each pixel using equations (6), (7), and (8) as above.

Figure 2:
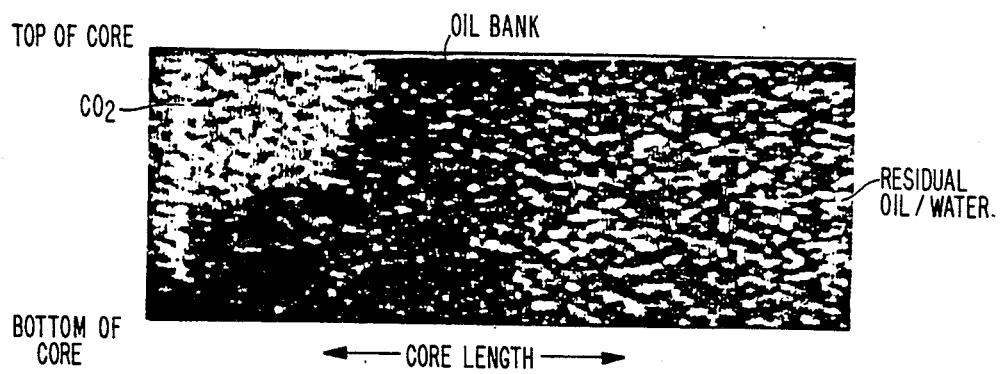
FIG. 2 is a pictorial representation of the fluid saturations shown in FIG. 1.

FIG. 1 shows the saturations obtained from CAT measurements of a first-contact miscible $CO_2$ flood at 3000 psi and 77° C. using a Berea sandstaone as the core. FIG. 2 shows the same saturation as a pictorial representation. In FIG. 2 the light areas are oil, the dark areas brine and the second dark area at the left is $CO_2$ which is dispersed through the oil bank.

Figure 3:
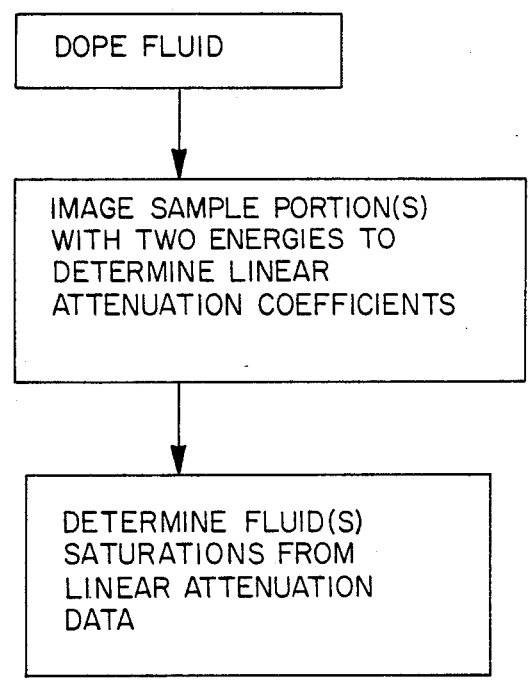
FIG. 3 shows a simplified flow chart of the basic method of the present invention.

FIG. 3 shows a simplified flow chart of the basic method of the present invention.

What is claimed is:

1. A method for determining the saturations of a plurality of fluids in a sample of porous material with an X-ray Computerized Axial Tomography (CAT) apparatus, comprising:
   doping a preselected fluid with an X-ray absorbing material,
   imaging such a sample in such a CAT apparatus employing at least two different preselected mean energy levels for at least a portion of such a sample to determine linear attenuation coefficient data for said fluids in said at least a portion of such sample at said preselected energies, and
   determining the saturations of each of said fluids in said at least a portion of such a sample from said data.

2. A method as described in claim 1, further comprising:
   determining fully saturated linear attenuation coefficients for each of said fluids at said preselected energies from said data, and
   wherein said step of determining the saturations of each of said fluids from said data further comprises determining said saturations from said fully saturated linear attenuation coefficients and from said data.

3. A method as described in claim 2, further comprising:
   measuring effluent data for each of said fluids, and
   wherein said step of determining the saturations of said fluids from said data further comprises determining said saturations from said data, said fully saturated linear attenuation coefficients, or said effluent data, or from combinations thereof.

4. A method as described in claim 2, wherein said step of determining the saturations of each of said fluids from said data employs the following equations:

$$\mu_1 = \mu_{a1}S_a + \mu_{b1}S_b + \mu_{c1}S_c$$

$$\mu_2 = \mu_{a2}S_a + \mu_{b2}S_b + \mu_{c2}S_c$$

$$1 = S_a + S_b + S_c$$

where the subscripts 1 and 2 refer to the two preselected mean X-ray energies, the subscripts a, b, and c refer to fluids a, b, and c, respectively, $\mu$ with one subscript is a measured linear attenuation coefficient, $\mu$ with two subscripts is a fully saturated linear attenuation coefficient, and S is a fluid saturation.

5. A method as described in claim 4, wherein said fluids a, b, and c comprise oil, brine, and gas, respectively.

6. A method for determining the saturations of a plurality of fluids in a sample of porous material employed to simulate an enhanced oil recovery process with an X-ray Computerized Axial Tomography (CAT) apparatus, comprising:
   doping a preselected fluid with an X-ray absorbing material,
   imaging such a sample during said simulation of such a process in such a CAT apparatus employing at least two different preselected mean energy levels for at least a portion of such a sample to determine linear attenuation coefficient data for said fluids in said at least a portion of such sample at said preselected energies, and
   determining the saturations of each of said fluids in said at least a portion of such a sample from said data.

7. A method as described in claim 6, wherein said simulation comprises:
   providing a suitable vessel to allow such a sample to be subjected to preselected reservoir conditions.

8. A method as described in claim 6, wherein said simulation comprises:
   subjecting such a sample to preselected reservoir conditions.

9. A method for determining the saturation of a fluid in a sample of porous material with an X-ray Computerized Axial Tomography (CAT) apparatus, comprising:
   doping such a fluid with an X-ray absorbing material,
   imaging such a sample in such a CAT apparatus employing at least two different preselected mean energy levels for at least one preselected volume of such a sample to determine linear attenuation coefficient data for such a fluid in said at least one preselected volume at said preselected energies, and
   determining the saturation of such a fluid in said at least one preselected volume from said data.

10. A method for determining the saturations of a plurality of fluids during fluid flow in a sample of porous material with an X-ray Computerized Axial Tomography (CAT) apparatus, comprising:
   doping a preselected fluid with an X-ray absorbing material,
   imaging such a sample in such a CAT apparatus employing at least two different preselected mean energy levels for at least a portion of such a sample to determine linear attenuation coefficient data for said fluids in said at least a portion of such sample at said preselected energies, and
   determining the saturations of each of said fluids in said at least a portion of such a sample from said data.

* * * * *